(12) United States Patent
Suh et al.

(10) Patent No.: US 11,396,511 B2
(45) Date of Patent: Jul. 26, 2022

(54) SUBSTITUTED 9,13B-DIHYDRO-1H-DIBENZO[C,F]IMIDAZO[1,5-A]AZEPIN-3-YLBENZAMIDES AS ANTI-INFLAMMATORY AND ANALGESIC AGENTS

(71) Applicant: FRONTBIO CO., LTD., Chuncheon-si (KR)

(72) Inventors: Hong Won Suh, Chuncheon-si (KR); Jae Yong Lee, Chuncheon-si (KR); Soon Sung Lim, Chuncheon-si (KR); Jeong Tae Lee, Seoul (KR); Seung Hwan Hwang, Namyangju-si (KR); Sang Pil Jang, Seoul (KR); Sung Hwan Park, Guri-si (KR); Jeong Ho Jeon, Anseong-si (KR); Hyun Min Lim, Uijeongbu-si (KR); Ju Mi Lee, Chuncheon-si (KR)

(73) Assignee: FRONTBIO CO., LTD., Chuncheon-si (KR)

( * ) Notice: Subject to any disclaimer, the term of this patent is extended or adjusted under 35 U.S.C. 154(b) by 99 days.

(21) Appl. No.: 16/770,552

(22) PCT Filed: Dec. 11, 2018

(86) PCT No.: PCT/KR2018/015699
§ 371 (c)(1),
(2) Date: Jun. 5, 2020

(87) PCT Pub. No.: WO2019/117592
PCT Pub. Date: Jun. 20, 2019

(65) Prior Publication Data
US 2020/0369668 A1    Nov. 26, 2020

(30) Foreign Application Priority Data

Dec. 12, 2017   (KR) .................. 10-2017-0170098

(51) Int. Cl.
*C07D 487/06* (2006.01)
*C07D 487/04* (2006.01)

(52) U.S. Cl.
CPC .................. *C07D 487/04* (2013.01)

(58) Field of Classification Search
CPC .................................................. C07D 487/06
USPC ....................................................... 540/579
See application file for complete search history.

(56) References Cited

U.S. PATENT DOCUMENTS

| 3,725,429 A | 4/1973 | Brown et al. |
| 4,313,931 A | 2/1982 | Walther et al. |
| 5,942,503 A | 8/1999 | Jung et al. |
| 8,828,979 B2 | 9/2014 | Gerlach et al. |

FOREIGN PATENT DOCUMENTS

| JP | 2000500446 A | 1/2000 |
| JP | 2001064282 A | 3/2001 |
| JP | 2013151484 A | 8/2013 |
| WO | 2009109501 A2 | 9/2009 |
| WO | 2012032509 A2 | 3/2012 |

OTHER PUBLICATIONS

Borer, L. et al., "Experiments with Aspirin," Journal of Chemical Education, vol. 77, No. 3, Mar. 2000, 2 pages.
Vu, C. et al., "Synthesis and Characterization of Fatty Acid Conjugates of Niacin and Salicylic Acid," Journal of Medicinal Chemistry, vol. 59, No. 3, Feb. 11, 2016, Available Online Feb. 1, 2016, 15 pages.
ISA Korean Intellectual Property Office, International Search Report Issued in Application No. PCT/KR2018/015699, dated Mar. 18, 2019, WIPO, 5 pages.

*Primary Examiner* — Douglas M Willis
(74) *Attorney, Agent, or Firm* — McCoy Russell LLP

(57) ABSTRACT

The present invention relates to compounds of [Formula A]:

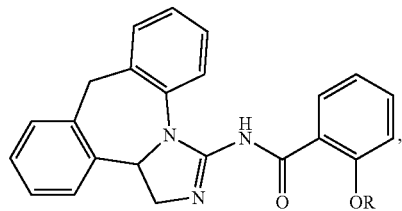

including N-(9,13b-dihydro-1H-dibenzo[c,f]imidazo[1,5-a]azepin-3-yl)-2-hydroxybenzamide, 2-((9,13b-dihydro-1H-dibenzo[c,f]imidazo[1,5-a]azepin-3-yl)carbamoyl)phenyl acetate, methods for preparing the compounds, and compositions including the compounds as active ingredients. The compounds of the present invention are very effective in anti-inflammation and pain relief. The compositions of the present invention are effective in preventing or treating inflammation and/or pain.

10 Claims, 10 Drawing Sheets

SUBSTITUTED 9,13B-DIHYDRO-1H-DIBENZO[C,F]IMIDAZO[1,5-A]AZEPIN-3-YLBENZAMIDES AS ANTI-INFLAMMATORY AND ANALGESIC AGENTS

CROSS-REFERENCE TO RELATED APPLICATIONS

The present application is a U.S. National Phase of International Patent Application Serial No. PCT/KR2018/015699 entitled "COMPOUND OF N-(9,13B-DIHYDRO-1H-DIBENZO[C,F]IMIDAZO [1,5-A]AZEPINE-3-YL)-2-HYDROXYBENZAMIDE AND 2-((9,13B-DIHYDRO-1H-DIBENZO [C,F[IMIDAZO [1,5-A]AZEPINE-3-YL) CARB AMOYL)PHENYL ACETATE, PREPARATION METHOD THEREFOR, AND ANTI-INFLAMMATORY AND ANALGESIC AGENT CONTAINING SAME," filed on Dec. 11, 2018. International Patent Application Serial No. PCT/KR2018/015699 claims priority to Korean Patent Application No. 10-2017-0170098 filed on Dec. 12, 2017. The entire contents of each of the above-referenced applications are hereby incorporated by reference for all purposes.

TECHNICAL FIELD

The present invention relates to N-(9,13b-dihydro-1H-dibenzo[c,f]imidazo[1,5-a]azepin-3-yl)-2-hydroxybenzamide, 2-((9,13b-dihydro-1H-dibenzo[c,f]imidazo[1,5-a]azepin-3-yl)carbamoyl)phenyl acetate, methods for preparing the compounds, and compositions including the compounds.

BACKGROUND AND SUMMARY

According to the definition by the International Association for the Study of Pain (IASP), pain is defined as "an unpleasant sensory and emotional experience associated with actual or potential tissue damage, or described in terms of such damage. Pain can be largely divided into three types of pain: nociceptive, inflammatory and neuropathic pain. Such pain includes sensory and emotional aspects of pain and people have unique, individual responses to the same stimulus.

Pain is usually caused by the activity of primary nociceptive receptors upon actual or potential tissue damage. Nociceptive receptors are organs that do not exist separately but are present in the form of free nerve endings of peripheral sensory nerves between epidermal cells, unlike other sensory receptors. The cell bodies of peripheral neurons are cells that are located in the dorsal root ganglia next to the spinal cord to transmit pain and have a long dendrite and a short one running to the spinal cord. Synapses and neurotransmitters are present between neurons play leading roles in pain generation and transmission. Stimulation of nociceptive receptors is perceived by the cerebral cortex after transduction, transmission, and modulation in the limbic system. That is, tissue damage causes an inflammatory response in nociceptive receptors and this inflammatory response leads to stimulation of the nociceptive receptors. The stimulation of the nociceptive receptors generates action potentials, which are transmitted through axons to stimulate neuronal bodies located in the dorsal root ganglia. Neurons in the dorsal root ganglia transmit action potentials through axons running toward the spinal cord, and finally, the action potentials reach nerve endings located in the spinal cord dorsal horn. In the nerve endings, neurotransmitters are secreted into synapses to stimulate secondary neurons and transmit pain signals to the brain. Glutamate is considered to play a major role as a neurotransmitter. In the spinal cord, primary sensory neurons form synapses with many interneurons as well as with secondary sensory neurons.

Pathways for algesia transmission are relatively well known neuroanatomically but their mechanisms and the mechanisms of symptom relief and analgesia are still unknown. Particularly, chronic pain is one of the most debilitating conditions in human life. Efforts to solve the problems of chronic pain have been made since human history began and many scientists have attempted to elucidate the mechanism of chronic pain and treat chronic pain. However, various pathogenetic factors cause pain and thus the mechanisms causing algesia are different. Further, appropriate animal models necessary for pain studies are not established. For these reasons, no satisfactory solutions have yet been found although considerable research has concentrated.

Inflammation is a series of symptoms that involve symptoms such as redness, edema, heat sensation, and pain by vasodilation, blood exudation, migration of inflammatory cells, and sensitization of nociceptive receptors. In humans, rheumatoid arthritis, bacterial infection, and other inflammatory diseases are known to be important factors in the expression of chronic pain. Patients whose inflammatory pain persists and turns into chronic pain suffer from mental and social afflictions as well as direct pain. Thus, inflammatory pain requires immediate and active treatment. However, there are difficulties in treating inflammatory pain due to a lack of effective therapies or therapeutics.

One of the oldest models for pain studies is associated with inflammation. When inflammation is caused, many kinds of chemical mediators such as prostaglandin, histamine, bradykinin, serotonin, interleukin-1, interleukin-6, and substance P are liberated from inflammatory cells, damaged tissue, and nerve endings in tissue to cause anatomical and physiological changes of the tissue and activate nociceptors to induce algesia. Such acute pain is considered to cause internal modification of the nervous system, leading to persistent pain.

Neuropathic pain is refractory pain caused by damage or functional abnormality of the nervous system and persists chronically. Patients with such pain considerably lose their quality of life. Pain causes sleep disturbance and emotional disorders such as depression and even social problems such as low productivity by poor social adaptability.

In attempts to relieve or suppress pain, a pharmaceutical composition for the treatment of pain including epinastine is known in U.S. Pat. No. 5,942,503 and the effect of salicylic acid on pain relief is known in U.S. Pat. No. 8,828,979. Non-steroidal anti-inflammatory drugs (NSAIDs) are generally used to suppress pain and examples thereof include aspirin, ibuprofen, and ketoprofen. However, NSAIDs are limited in their use due to their potential side effects such as gastrointestinal disorders and bleeding. Further, therapies for neuropathic pain are mainly based on the modulation of activity of ion channels in the peripheral or central nervous system (gabapentin, pregabalin, lidocaine, etc.) and the enhancement of endogenous inhibitory mechanisms (TCA, duloxetine, and opioid drugs). Many drugs are known to be effective for neuropathic pain but their effects are still unsatisfactory.

Thus, there is a need to develop analgesic compositions including novel compounds that are effective in suppressing inflammation or relieving pain without side effects. There is no disclosure in the prior art regarding the effects of compounds synthesized in the present invention on inflammation suppression and pain relief.

DISCLOSURE

Technical Problem

The present invention has been made in an effort to solve the problems of the prior art and it is an object of the present invention to provide compounds that are very effective in anti-inflammation and pain relief and methods for preparing the compounds.

Another object of the present invention is to provide compositions for preventing or treating inflammation and/or pain including any of the compounds as an active ingredient.

The present invention provides a compound represented by Formula A:

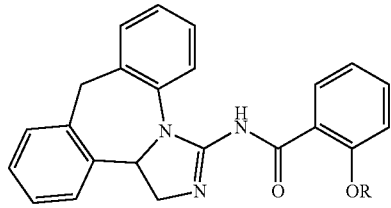

[Formula A]

wherein R is selected from the group consisting of hydrogen, $C_1$-$C_5$ alkyl, and $C_1$-$C_5$ alkylcarbonyl, or a pharmaceutically acceptable salt thereof.

In one embodiment of the present invention, the compound is selected from the group consisting of:
(1) N-(9,13b-dihydro-1H-dibenzo[c,f]imidazo[1,5-a]azepin-3-yl)-2-hydroxybenzamide (E-S); and
(2) 2-((9,13b-dihydro-1H-dibenzo[c,f]imidazo[1,5-a]azepin-3-yl)carbamoyl)phenyl acetate (E-A).

The present invention also provides a pharmaceutical composition for preventing or treating pain including a therapeutically effective amount of the compound represented by Formula A or pharmaceutically acceptable salt thereof.

Exemplary embodiments of the present invention will now be described with reference to the accompanying drawings. In the following description, numerous specific details, for example, specific structures, compositions, and processes, are set forth to provide a full understanding of the invention. However, specific embodiments can be implemented without one or more of these specific details or with other known methods or structures. In other instances, known processes and production techniques are not described in particular detail to avoid unnecessarily obscuring the invention. Reference throughout this specification to "one embodiment" or "an embodiment" means that a particular feature, structure, composition, or characteristic described in connection with the embodiment is included in at least one embodiment. Thus, the appearances of the phrases "in one embodiment" or "in an embodiment" in various places throughout this specification are not necessarily all referring to the same embodiment.

Furthermore, the particular features, structures, compositions, or characteristics may be combined in any suitable manner in one or more embodiments.

Unless otherwise defined, all terms (including technical and scientific terms) used herein have the same meaning as commonly understood by those skilled in the art to which the present invention belongs.

As used herein, the term "alkyl", by itself or as part of another substituent, means a straight or branched chain hydrocarbon radical, having the number of carbon atoms designated. For example, "$C_1$-$C_{10}$ alkyl" refers to a straight or branched chain hydrocarbon radical containing 1 to 10 carbon atoms that is derived by the removal of one hydrogen atom from a single carbon atom of a parent alkane. Unless the context clearly indicates otherwise, the term "alkyl" refers to "$C_1$-$C_{10}$ alkyl", preferably "$C_1$-$C_5$ alkyl".

As used herein, the term "alkylcarbonyl", by itself or as part of another substituent, means an acyl group derived from an alkanecarboxylic acid, i.e. alkyl-C(O)—, such as acetyl, propionyl, butyryl, valeryl, 4-methylvaleryl. Unless the context clearly indicates otherwise, the term "alkylcarbonyl" refers to "$C_1$-$C_{10}$ alkylcarbonyl", preferably "$C_1$-05 alkylcarbonyl".

The present invention provides a compound represented by Formula A:

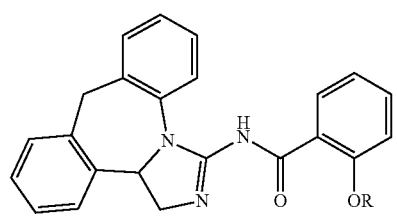

[Formula A]

wherein R is selected from the group consisting of hydrogen, $C_1$-$C_5$ alkyl, and $C_1$-$C_5$ alkylcarbonyl, or a pharmaceutically acceptable salt thereof.

In one embodiment of the present invention, the compound is selected from the group consisting of:
(1) N-(9,13b-dihydro-1H-dibenzo[c,f]imidazo[1,5-a]azepin-3-yl)-2-hydroxybenzamide (E-S); and
(2) 2-((9,13b-dihydro-1H-dibenzo[c,f]imidazo[1,5-a]azepin-3-yl)carbamoyl)phenyl acetate (E-A).

The present invention also provides a pharmaceutical composition for preventing or treating pain including a therapeutically effective amount of the compound represented by Formula A or pharmaceutically acceptable salt thereof.

In one embodiment of the present invention, the pain is selected from nociceptive pain, invasive pain, psychogenic pain, inflammatory pain, pathologic pain, neuropathic pain, cancer pain, postoperative pain, trigeminal neuralgia, idiopathic pain, diabetic neuropathic pain, and migraine but is not limited thereto.

The present invention also provides a pharmaceutical composition for preventing or treating inflammation including a therapeutically effective amount of the compound represented by Formula A or pharmaceutically acceptable salt thereof.

In one embodiment of the present invention, the pharmaceutical composition further includes one or more additives selected from the group consisting of, but not limited to, pharmaceutically acceptable carriers, excipients, pH adjusting agents, stabilizers, preservatives, sweeteners, and flavors.

In one embodiment of the present invention, the pharmaceutical composition is prepared into a formulation selected from the group consisting of, but not limited to, eye drops, injection solutions, granules, tablets, pills, capsules, gels, syrups, suspensions, emulsions, drips, and liquids.

The term "prevention" or "preventing" as used herein means all actions that suppress or delay the onset of inflammation and/or pain by administration of the composition according to the present invention.

The term "treatment" or "treating" as used herein means all actions that ameliorate or beneficially change a symptom associated with inflammation and/or pain by administration of the composition according to the present invention.

The term "pharmaceutically effective amount" as used herein refers to an amount sufficient to achieve efficacies and activities for preventing, ameliorating or treating pain.

The term "racemate" as used herein refers to a mixture that contains an equal amount of two enantiomers of different stereo-configurations and lacks optical activity.

The term "enantiomers" as used herein refers to two stereoisomers of a compound which are non-superimposable mirror images of one another.

The term "diastereomer" as used herein refers to stereoisomers that are not enantiomers, which occurs when two or more stereoisomers of a compound have different configurations at one or more (but not all) of the equivalent chiral centers and thus are not mirror images of each other.

In one embodiment of the present invention, the compounds of the present invention include racemates, enantiomers, diastereomers, mixtures of enantiomers or mixtures of diastereomers but are not limited to any particular stereochemistry.

The present invention provides a method for preparing the compound represented by Formula 3:

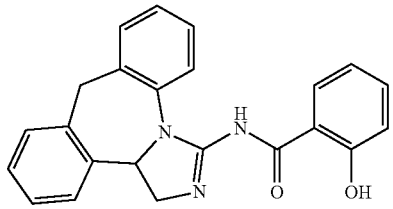

[Formula 3]

the method including 1) dissolving the compound represented by Formula 2:

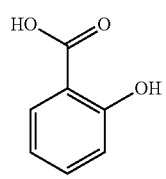

[Formula 2]

in a solvent, 2) adding the compound represented by Formula 1:

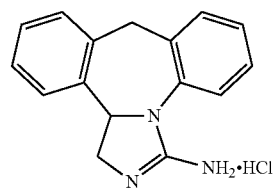

[Formula 1]

to the solution to couple the compound of Formula 1 with the compound of Formula 2, 3) further adding a base to the reaction mixture, and 4) further adding a coupling agent used in the coupling reaction.

In one embodiment of the present invention, the solvent is selected from the group consisting of DCM, $CH_3CN$, and $CHCl_3$ but is not limited thereto. $CHCl_3$ is most preferably used as the solvent.

In one embodiment of the present invention, the base is selected from the group consisting of DIPEA and TEA but is not limited thereto. TEA is most preferably used as the base.

In one embodiment of the present invention, the coupling agent is selected from the group consisting of DCC, HATU, and EDCI but is not limited thereto. EDCI is most preferably used as the coupling agent.

The present invention also provides a method for preparing the compound represented by Formula 4:

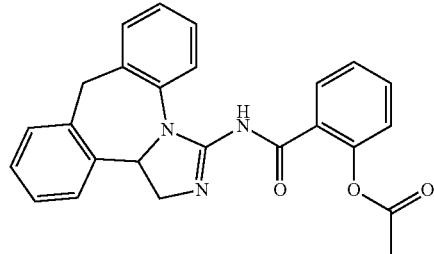

[Formula 4]

the method including 1) reacting the compound represented by Formula 3:

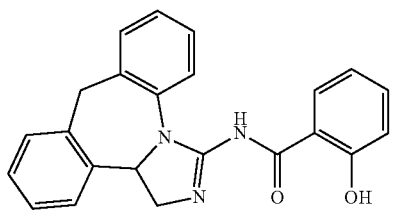

[Formula 3]

with acetic anhydride in the presence of an acid catalyst.

The pharmaceutically acceptable salt of the present invention can be prepared by any suitable method known in the art. Examples of such pharmaceutically acceptable salts include, but are not limited to: salts formed from inorganic acids such as hydrochloric acid, hydrobromic acid, sulfuric acid, sodium bisulfate, phosphoric acid, nitric acid, and carbonic acid; salts formed from organic acids such as formic acid, acetic acid, propionic acid, oxalic acid, succinic acid, benzoic acid, citric acid, maleic acid, malonic acid, tartaric acid, gluconic acid, lactic acid, gentisic acid, fumaric acid, lactobionic acid, salicylic acid, trifluoroacetic acid, and acetylsalicylic acid (aspirin); salts formed from amino acids such as glycine, alanine, valine, isoleucine, serine, cysteine, cystine, aspartic acid, glutamine, lysine, arginine, tyrosine, and proline; salts formed from sulfonic acids such as methanesulfonic acid, ethanesulfonic acid, benzenesulfonic acid, and toluenesulfonic acid; metal salts formed by reaction with alkali metals such as sodium, lithium, and potassium; and salts formed from ammonium ions.

Each of the pharmaceutical compositions of the present invention includes at least one pharmaceutically acceptable carrier in addition to the corresponding active ingredient. The pharmaceutically acceptable carrier may be any of those that are usually used in pharmaceutical compositions. Examples of such pharmaceutically acceptable carriers include, but are not limited to, lactose, dextrose, sucrose, sorbitol, mannitol, starch, gum acacia, potassium phosphate, alginate, gelatin, potassium silicate, microcrystalline cellulose, polyvinylpyrrolidone, cellulose, water, syrup, methylcellulose, methyl hydroxybenzoate, propyl hydroxybenzoate, talc, magnesium stearate, and mineral oil. Each of the pharmaceutical composition of the present invention may further include one or more additives selected from the group consisting of lubricating agents, wetting agents, sweetening agents, flavoring agents, emulsifying agents, suspending agents, and preservatives. Details of suitable pharmaceutically acceptable carriers and formulations can be found in Remington's Pharmaceutical Sciences ($19^{th}$ ed., 1995).

Examples of suitable excipients that can be used in the pharmaceutical composition of the present invention include sweeteners, binders, solubilizers, solubilization aids, wetting agents, emulsifiers, isotonic agents, adsorbents, disintegrants, antioxidants, preservatives, lubricants, fillers, and flavoring agents. The excipients may be, for example, lactose, dextrose, sucrose, mannitol, sorbitol, cellulose, glycine, silica, magnesium aluminum silicate, starch, gelatin, gum tragacanth, arginine acid, sodium alginate, methylcellulose, sodium carboxymethylcellulose, water, ethanol, polyethylene glycol, polyvinylpyrrolidone, sodium chloride, calcium chloride, orange essence, strawberry essence, and vanilla flavor.

For use of the compounds according to the present invention as drugs, the compositions are prepared in the form of pharmaceutical agents and contain suitable pharmaceutical organic or inorganic inert vehicles in addition to the corresponding active ingredients for oral or parenteral administration. The inert vehicles may be, for example, water, gelatin, gum arabic, lactose, starch, vegetable oils, and polyalkylene glycol. The pharmaceutical agents may be in solid forms, for example, as tablets, dragees, suppositories or capsules or in liquid forms, for example, as solutions, suspensions or emulsions. The pharmaceutical agents optionally further contain adjuvants, such as preservatives, stabilizers, wetting agents or emulsifiers, salts for changing the osmotic pressure or buffers.

For oral administration, tablets, dragees or capsules containing talc and/or hydrocarbon vehicles or binders, for example, lactose, corn or potato starch, are suitable. The liquid forms may be, for example, sweetener-containing juices. For parenteral administration, particularly preferred are injection solutions or suspensions that can be administered intravenously, subcutaneously, intramuscularly, intraperitoneally, transdermally or intra-articularly. More specifically, the compositions of the present invention are administered intra-articularly or intraperitoneally.

The dose of the compound represented by Formula A may vary depending on the general health, age, body weight, and sex of patients, the mode of administration, and the severity of disease. The daily dose of the compound represented by Formula A is generally from 0.1 mg to 2000 mg for an adult patient weighing 70 kg. The compound of the present invention can be administered in a single dose or in divided doses per day. However, the scope of the present invention is not limited to the above-proposed dose.

Advantageous Effects

The compounds of the present invention are very effective in preventing and treating inflammation and/or pain. The methods of the present invention are suitable for preparing the compounds.

The compositions of the present invention are effective in preventing and treating inflammation and/or pain due to the presence of the compounds as active ingredients.

The compounds of the present invention can be prepared in high yields by the methods. The compositions including the compounds of the present invention are effective in anti-inflammation and/or pain relief.

DETAILED DESCRIPTION

Best Mode

Figure 1:
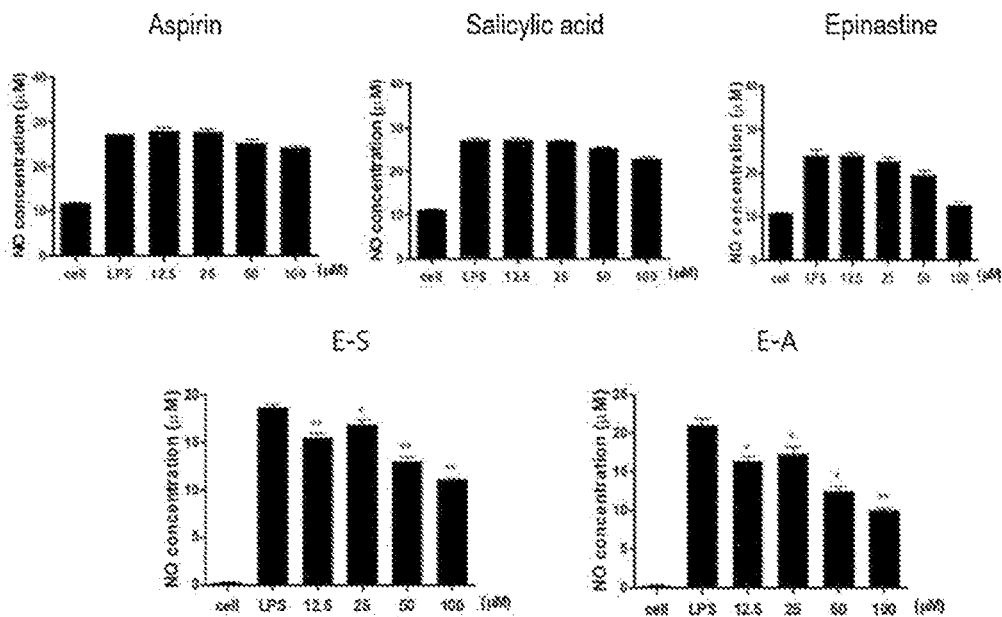
FIG. 1 shows the amounts of NO produced from cells when treated with the compounds prepared in Preparative Examples 1 and 2.

Exemplary embodiments of the present invention will now be described with reference to the accompanying drawings. In the following description, numerous specific details, for example, specific structures, compositions, and processes, are set forth to provide a full understanding of the invention. However, specific embodiments can be implemented without one or more of these specific details or with other known methods or structures. In other instances, known processes and production techniques are not described in particular detail to avoid unnecessarily obscuring the invention. Reference throughout this specification to "one embodiment" or "an embodiment" means that a particular feature, structure, composition, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, compositions, or characteristics may be combined in any suitable manner in one or more embodiments.

Unless otherwise defined, all terms (including technical and scientific terms) used herein have the same meaning as commonly understood by those skilled in the art to which the present invention belongs.

As used herein, the term "alkyl", by itself or as part of another substituent, means a straight or branched chain hydrocarbon radical, having the number of carbon atoms designated. For example, "$C_1$-$C_{10}$ alkyl" refers to a straight or branched chain hydrocarbon radical containing 1 to 10 carbon atoms that is derived by the removal of one hydrogen atom from a single carbon atom of a parent alkane. Unless the context clearly indicates otherwise, the term "alkyl" refers to "$C_1$-$C_{10}$ alkyl", preferably "$C_1$-$C_5$ alkyl".

As used herein, the term "alkylcarbonyl", by itself or as part of another substituent, means an acyl group derived from an alkanecarboxylic acid, i.e. alkyl-C(O)—, such as acetyl, propionyl, butyryl, valeryl, 4-methylvaleryl. Unless the context clearly indicates otherwise, the term "alkylcarbonyl" refers to "$C_1$-$C_{10}$ alkylcarbonyl", preferably "$C_1$-$C_5$ alkylcarbonyl".

The present invention provides a compound represented by Formula A:

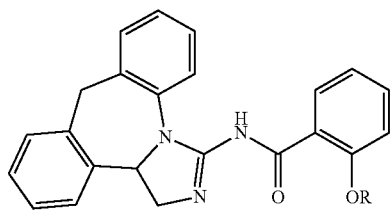

[Formula A]

wherein R is selected from the group consisting of hydrogen, $C_1$-$C_5$ alkyl, and $C_1$-$C_5$ alkylcarbonyl, or a pharmaceutically acceptable salt thereof.

In one embodiment of the present invention, the compound is selected from the group consisting of:
(1) N-(9,13b-dihydro-1H-dibenzo[c,f]imidazo[1,5-a]azepin-3-yl)-2-hydroxybenzamide (E-S); and
(2) 2-((9,13b-dihydro-1H-dibenzo[c,f]imidazo[1,5-a]azepin-3-yl)carbamoyl)phenyl acetate (E-A).

The present invention also provides a pharmaceutical composition for preventing or treating pain including a therapeutically effective amount of the compound represented by Formula A or pharmaceutically acceptable salt thereof.

In one embodiment of the present invention, the pain is selected from nociceptive pain, invasive pain, psychogenic pain, inflammatory pain, pathologic pain, neuropathic pain, cancer pain, postoperative pain, trigeminal neuralgia, idiopathic pain, diabetic neuropathic pain, and migraine but is not limited thereto.

The present invention also provides a pharmaceutical composition for preventing or treating inflammation including a therapeutically effective amount of the compound represented by Formula A or pharmaceutically acceptable salt thereof.

In one embodiment of the present invention, the pharmaceutical composition further includes one or more additives selected from the group consisting of, but not limited to, pharmaceutically acceptable carriers, excipients, pH adjusting agents, stabilizers, preservatives, sweeteners, and flavors.

In one embodiment of the present invention, the pharmaceutical composition is prepared into a formulation selected from the group consisting of, but not limited to, eye drops, injection solutions, granules, tablets, pills, capsules, gels, syrups, suspensions, emulsions, drips, and liquids.

The term "prevention" or "preventing" as used herein means all actions that suppress or delay the onset of inflammation and/or pain by administration of the composition according to the present invention.

The term "treatment" or "treating" as used herein means all actions that ameliorate or beneficially change a symptom associated with inflammation and/or pain by administration of the composition according to the present invention.

The term "pharmaceutically effective amount" as used herein refers to an amount sufficient to achieve efficacies and activities for preventing, ameliorating or treating pain.

The term "racemate" as used herein refers to a mixture that contains an equal amount of two enantiomers of different stereo-configurations and lacks optical activity.

The term "enantiomers" as used herein refers to two stereoisomers of a compound which are non-superimposable mirror images of one another.

The term "diastereomer" as used herein refers to stereoisomers that are not enantiomers, which occurs when two or more stereoisomers of a compound have different configurations at one or more (but not all) of the equivalent chiral centers and thus are not mirror images of each other.

In one embodiment of the present invention, the compounds of the present invention include racemates, enantiomers, diastereomers, mixtures of enantiomers or mixtures of diastereomers but are not limited to any particular stereochemistry.

The present invention provides a method for preparing the compound represented by Formula 3:

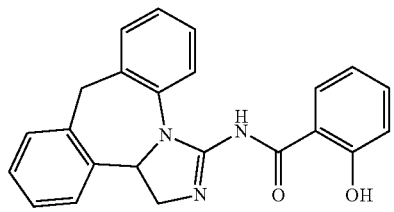

[Formula 3]

the method including 1) dissolving the compound represented by Formula 2:

in a solvent, 2) adding the compound represented by Formula 1:

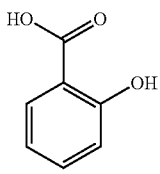
[Formula 2]

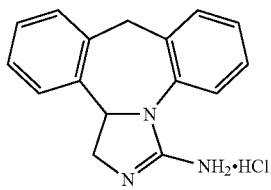
[Formula 1]

to the solution to couple the compound of Formula 1 with the compound of Formula 2, 3) further adding a base to the reaction mixture, and 4) further adding a coupling agent used in the coupling reaction.

In one embodiment of the present invention, the solvent is selected from the group consisting of DCM, $CH_3CN$, and $CHCl_3$ but is not limited thereto. $CHCl_3$ is most preferably used as the solvent.

In one embodiment of the present invention, the base is selected from the group consisting of DIPEA and TEA but is not limited thereto. TEA is most preferably used as the base.

In one embodiment of the present invention, the coupling agent is selected from the group consisting of DCC, HATU, and EDCI but is not limited thereto. EDCI is most preferably used as the coupling agent.

The present invention also provides a method for preparing the compound represented by Formula 4:

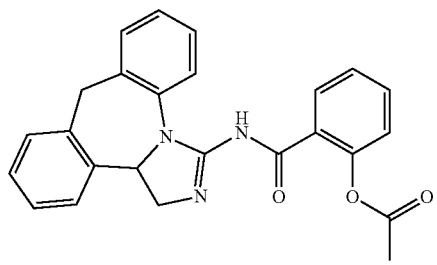
[Formula 4]

the method including 1) reacting the compound represented by Formula 3:

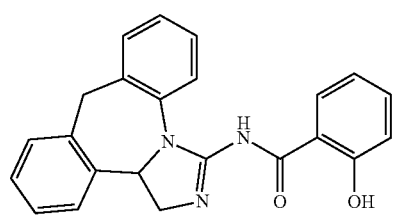
[Formula 3]

with acetic anhydride in the presence of an acid catalyst.

The pharmaceutically acceptable salt of the present invention can be prepared by any suitable method known in the art. Examples of such pharmaceutically acceptable salts include, but are not limited to: salts formed from inorganic acids such as hydrochloric acid, hydrobromic acid, sulfuric acid, sodium bisulfate, phosphoric acid, nitric acid, and carbonic acid; salts formed from organic acids such as formic acid, acetic acid, propionic acid, oxalic acid, succinic acid, benzoic acid, citric acid, maleic acid, malonic acid, tartaric acid, gluconic acid, lactic acid, gentisic acid, fumaric acid, lactobionic acid, salicylic acid, trifluoroacetic acid, and acetylsalicylic acid (aspirin); salts formed from amino acids such as glycine, alanine, valine, isoleucine, serine, cysteine, cystine, aspartic acid, glutamine, lysine, arginine, tyrosine, and proline; salts formed from sulfonic acids such as methanesulfonic acid, ethanesulfonic acid, benzenesulfonic acid, and toluenesulfonic acid; metal salts formed by reaction with alkali metals such as sodium, lithium, and potassium; and salts formed from ammonium ions.

Each of the pharmaceutical compositions of the present invention includes at least one pharmaceutically acceptable carrier in addition to the corresponding active ingredient. The pharmaceutically acceptable carrier may be any of those that are usually used in pharmaceutical compositions. Examples of such pharmaceutically acceptable carriers include, but are not limited to, lactose, dextrose, sucrose, sorbitol, mannitol, starch, gum acacia, potassium phosphate, alginate, gelatin, potassium silicate, microcrystalline cellulose, polyvinylpyrrolidone, cellulose, water, syrup, methylcellulose, methyl hydroxybenzoate, propyl hydroxybenzoate, talc, magnesium stearate, and mineral oil. Each of the pharmaceutical composition of the present invention may further include one or more additives selected from the group consisting of lubricating agents, wetting agents, sweetening agents, flavoring agents, emulsifying agents, suspending agents, and preservatives. Details of suitable pharmaceutically acceptable carriers and formulations can be found in Remington's Pharmaceutical Sciences (19$^{th}$ ed., 1995).

Examples of suitable excipients that can be used in the pharmaceutical composition of the present invention include sweeteners, binders, solubilizers, solubilization aids, wetting agents, emulsifiers, isotonic agents, adsorbents, disintegrants, antioxidants, preservatives, lubricants, fillers, and flavoring agents. The excipients may be, for example, lactose, dextrose, sucrose, mannitol, sorbitol, cellulose, glycine, silica, magnesium aluminum silicate, starch, gelatin, gum tragacanth, arginine acid, sodium alginate, methylcellulose, sodium carboxymethylcellulose, water, ethanol, polyethylene glycol, polyvinylpyrrolidone, sodium chloride, calcium chloride, orange essence, strawberry essence, and vanilla flavor.

For use of the compounds according to the present invention as drugs, the compositions are prepared in the form of pharmaceutical agents and contain suitable pharmaceutical organic or inorganic inert vehicles in addition to the corresponding active ingredients for oral or parenteral administration. The inert vehicles may be, for example, water, gelatin, gum arabic, lactose, starch, vegetable oils, and polyalkylene glycol. The pharmaceutical agents may be in solid forms, for example, as tablets, dragees, suppositories or capsules or in liquid forms, for example, as solutions, suspensions or emulsions. The pharmaceutical agents optionally further contain adjuvants, such as preservatives, stabilizers, wetting agents or emulsifiers, salts for changing the osmotic pressure or buffers.

For oral administration, tablets, dragees or capsules containing talc and/or hydrocarbon vehicles or binders, for example, lactose, corn or potato starch, are suitable. The liquid forms may be, for example, sweetener-containing juices. For parenteral administration, particularly preferred are injection solutions or suspensions that can be administered intravenously, subcutaneously, intramuscularly, intraperitoneally, transdermally or intra-articularly. More specifically, the compositions of the present invention are administered intra-articularly or intraperitoneally.

The dose of the compound represented by Formula A may vary depending on the general health, age, body weight, and sex of patients, the mode of administration, and the severity of disease. The daily dose of the compound represented by Formula A is generally from 0.1 mg to 2000 mg for an adult patient weighing 70 kg. The compound of the present invention can be administered in a single dose or in divided doses per day. However, the scope of the present invention is not limited to the above-proposed dose.

Mode for Invention

The present invention will be explained in more detail with reference to the following examples. It will be obvious to those skilled in the art that these examples are merely illustrative and are not intended to limit the scope of the present invention.

Materials and Methods

All reagents used in the present experiments were purchased from Aldrich, TCI, and Alfa aesar. Solvents were purchased from Junsei, Samchun, and Burdick & Jackson and were used without further purification. All glassware used for reactions were dried at 120° C. for at least 12 h before use. Proton nuclear magnetic resonance ($^1$H NMR) spectra and carbon-13 nuclear magnetic resonance ($^{13}$C NMR) spectra were recorded on a Varian Mercury TM 300 MHz FT-NMR for $^1$H and at 75 MHz for $^{13}$C using chemical shifts (δ) reported in parts per million (ppm) with TMS and coupling constants (J) expressed in Hz. CDCl$_3$, acetone-d$_6$, DMSO-d$_6$ and methanol-d$_4$ were used as NMR solvents and TMS was used as an internal standard. Flash chromatography was performed using silica gel (Merck 60, 230-400 mesh). Thin layer chromatography (TLC) was visualized using UV light (254 nm) on a glass backed silica gel plate (TLC silica gel 60 F254, Merck, layer thickness 0.2 mm) or was performed by treatment with p-anisaldehyde. Melting points were determined with a Mel-Temp II apparatus and are uncorrected. UV absorbance was determined on a Shimadzu UV-1800 spectrophotometer and IC$_{50}$ values of compounds were calculated using Origin 8 program. Mass spectra were obtained using Jeol JMS-700 (the Central Laboratory of Kangwon National University, South Korea). GC/MSD (gas chromatography/mass spectrometry) spectra were obtained on 7802A GC/5977E MSD (Agilent Technologies Inc.).

PREPARATIVE EXAMPLES

Synthesis of Compounds

Preparative Example 1

Synthesis of N-(9,13b-dihydro-1H-dibenzo[c,f]imidazo[1,5-a]azepin-3-yl)-2-hydroxybenzamide (E-S)

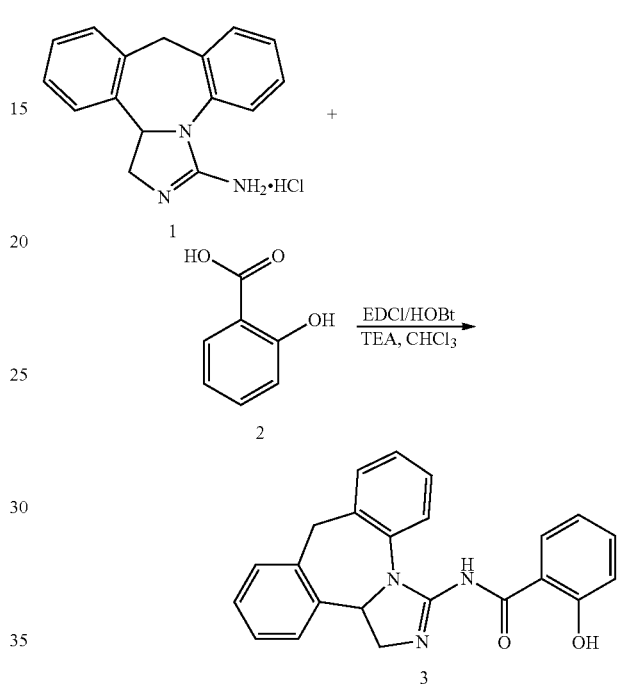

Salicylic acid 2 (0.36 g, 2.62 mmol) was dissolved in chloroform (10 mL) in a 100 mL round-bottom flask under an argon atmosphere, and then 1-hydroxybenzotriazole (HOBt) (0.47 g, 3.50 mmol) and 9,13b-dihydro-1H-dibenzo[c,f]imidazo[1,5-a]azepin-3-amine 1 (0.5 g, 1.75 mmol) were added thereto. To the mixture was added triethylamine (TEA) (0.52 mL, 3.85 mmol), followed by stirring for 30 min. The resulting mixture was slowly added with 1-ethyl-3-(3-dimethylaminopropyl)carbodiimide (EDCI) (0.67 g, 3.50 mmol). The temperature was gradually raised to room temperature over 12 h and stirring was continued at that temperature. After completion of the reaction, the reaction mixture was added with ethyl acetate (20 mL), washed with saturated sodium bicarbonate (NaHCO$_3$) (20 mL) and brine (20 mL), and dried over Na$_2$SO$_4$. The solvent was removed using a rotary evaporator. The residue was purified by column chromatography (hexane:ethyl acetate=4:1) to yield N-(9,13b-dihydro-1H-dibenzo[c,f]imidazo[1,5-a]azepin-3-yl)-2-hydroxybenzamide 3 (0.31 g, 0.84 mmol, 47.7%) as a white solid. $^1$H NMR (300 MHz, CDCl$_3$) δ: 3.50 (d, 1H, J=14.4 Hz), 3.70 (t, 1H, J=10.2 Hz), 4.25(t, 1H, J=9.6 Hz), 4.54 (d, 1H, J=14.4 Hz), 5.20 (t, 1H, J=10.2 Hz), 6.75 (d, 1H, J=7.5 Hz), 6.78 (d, 1H, J=7.5 Hz), 6.94 (t, 1H, J=4.3 Hz), 7.16-7.42 (m, 7H), 7.51 (d, 1H, J=7.8 Hz) 7.97 (d, 1H, J=8.4 Hz), 9.25 (s, 1H), 13.20 (s, 1H); $^{13}$C NMR (75 MHz, CDCl$_3$) δ: 38.7, 50.7, 60.8, 117.4, 118.1, 119.3, 127.2, 127.3, 127.7, 127.8, 127.9, 128.5, 128.7, 130.2, 130.4, 133.8, 135.0, 135.4, 135.5, 139.5, 160.8, 161.4; LRMS (Er) m/z (%): 369 ([M]+), 248 (base), 194, 121.

Synthesis Results

The yields of N-(9,13b-dihydro-1H-dibenzo[c,f]imidazo[1,5-a]azepin-3-yl)-2-hydroxybenzamide 3 were investigated when different coupling agents were used. The results are shown in Table 1. When salicylic acid 2 was coupled with 9,13b-dihydro-1H-dibenzo[c,f]imidazo[1,5-a]azepin-3-amine 1 using (N,N'-dicyclohexylcarboimide) (DCC) and triethylamine (TEA) or N,N-diisopropylethylamine (DIPEA), the yield was found to be low (16-17%). The combination of (1-[bis(dimethylamino)methylene]-1H-1,2,3-triazolo[4,5-b]pyridinium 3-oxide hexafluorophosphate) (HATU) with DIPEA led to a very low yield (2%). When EDCI and HOBt were used in combination with TEA for the coupling reaction, the solvent was found to have a great influence on the yield of the compound 3. After optimization of the reaction conditions, $CHCl_3$ was selected as the solvent under the final reaction conditions (yield 48%).

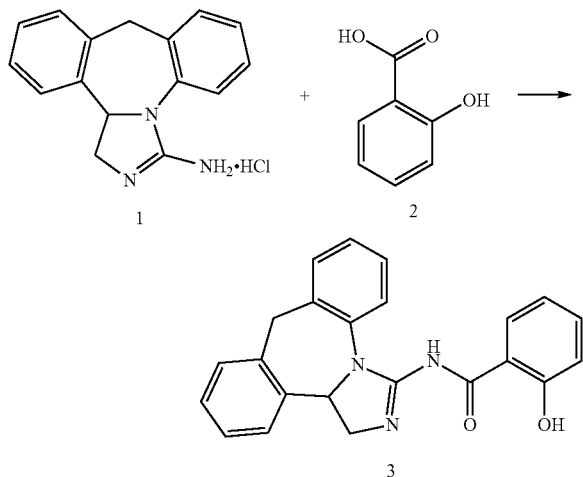

TABLE 1

Reaction conditions for the synthesis of N-(9,13b-dihydro-1H-dibenzo[c,f]imidazo[1,5-a]azepin-3-yl)-2-hydroxybenzamide 3

| Entry No. | Reagent | Base | Solvent | Yield |
|---|---|---|---|---|
| 1 | DCC | DIPEA | DCM | 17% |
| 2 | DCC | TEA | DCM | 16% |
| 3 | HATU | DIPEA | $CH_3CN$ | 2% |
| 4 | EDCI | TEA | DCM | 5% |
| 5 | EDCI | TEA | $CHCl_3$ | 48% |

Preparative Example 2

Synthesis of 2-((9,13b-dihydro-1H-dibenzo[c,f]imidazo[1,5-a]azepin-3-yl)carbamoyl)phenyl acetate (E-A)

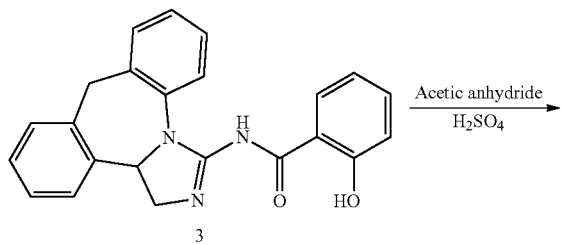

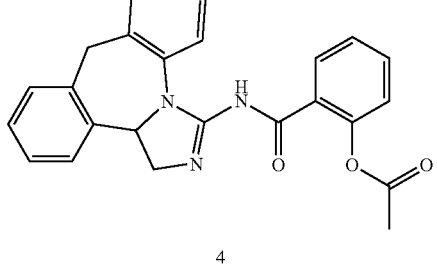

N-(9,13b-dihydro-1H-dibenzo[c,f]imidazo[1,5-a]azepin-3-yl)-2-hydroxybenzamide 3 (0.19 g, 0.51 mmol) was dissolved in acetic anhydride (0.44 mL) in a 100 mL round-bottom flask under an argon atmosphere, and then sulfuric acid ($H_2SO_4$) (0.05 mL, 3.50 mmol) was added thereto. The mixture was stirred at 70° C. for 1 h. Distilled water (5 mL) was added to quench the reaction. The reaction mixture was extracted with dichloromethane (20 mL) and dried over $Na_2SO_4$. The solvent was removed using a rotary evaporator. The residue was purified by column chromatography (hexane:ethyl acetate=4:1) to yield 2-((9,13b-dihydro-1H-dibenzo[c,f]imidazo[1,5-a]azepin-3-yl)carbamoyl)phenyl acetate 4 (0.10 g, 0.20 mmol, 38.5%) as a white solid. $^1$H NMR (300 MHz, $CDCl_3$) δ: 2.10 (s, 3H), 3.52 (d, 1H, J=14.4 Hz), 3.69 (t, 1H, J=10.7 Hz), 4.22 (t, 1H, J=9.5 Hz), 4.63 (d, 1H, J=14.1 Hz), 5.16 (t, 1H, J=10.7 Hz), 6.96 (d, 1H, J=8.4 Hz), 7.00 (d, 1H, J=3.9), 7.16-7.37 (m, 9H), 7.55 (d, 1H, J=7.8 Hz) 8.06 (d, 1H, J=7.8 Hz), 9.20 (s, 1H); $^{13}$C NMR (75 MHz, $CDCl_3$) δ: 21.0, 39.1, 50.0, 61.4, 123.1, 125.4, 127.2, 127.3, 127.4, 127.6, 127.8, 128.1, 130.3, 130.6, 131.6, 132.3, 135.6, 135.8, 136.9, 138.8, 150.3, 162.9, 169.7, 176.9; LRMS (EI$^+$) m/z (%): 411 ([M]$^+$), 369 (base), 339, 248.

Synthesis Results

Conditions for the synthesis of 2-((9,13b-dihydro-1H-dibenzo[c,f]imidazo[1,5-a]azepin-3-yl)carbamoyl)phenyl acetate 4 are shown in Table 2. Several coupling agents such as EDCI, HATU, and DCC were used but direct connection between the compound 1 and aspirin (route 1) failed to provide appropriate yields of the final product 4 (Entry Nos. 1, 2, and 3 of Table 2). Thus, the synthesis of the compound 4 started from the compound 3 (route 2). Simple acetylation of the phenolic —OH of the compound 3 using acetic anhydride was not achieved under basic conditions (Entry No. 4 of Table 2) but was achieved in a high yield of 39% under acidic conditions (No. 5 in Table 2).

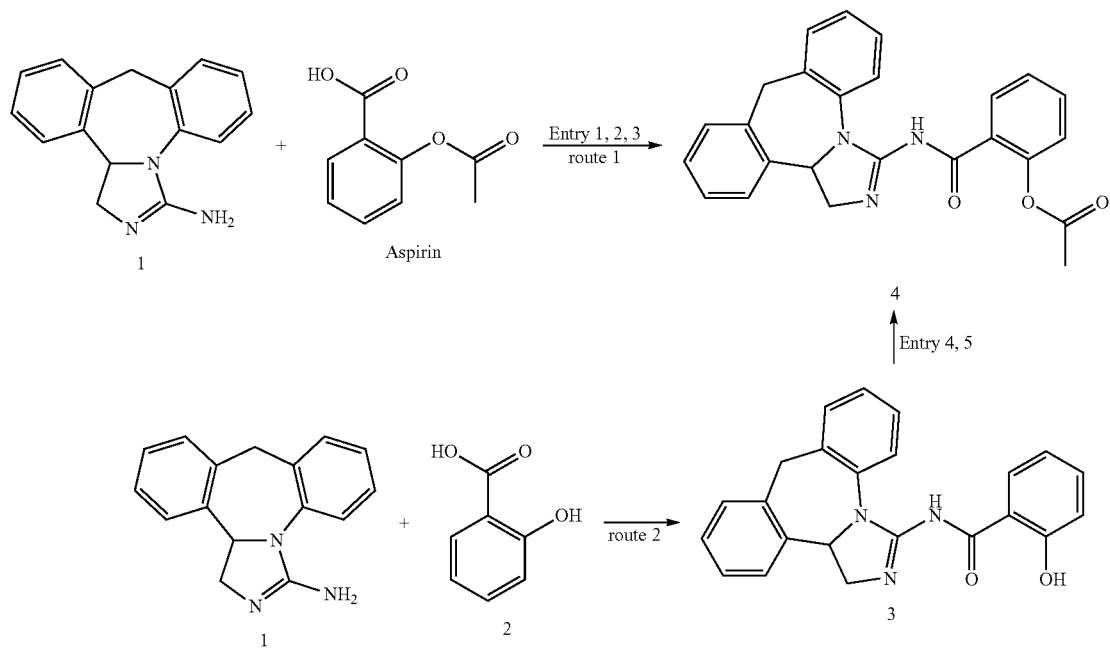

TABLE 2

Reaction conditions for the synthesis of 2-((9,13b-dihydro-1H-dibenzo[c,f]imidazo[1,5-a]azepin-3-yl)carbamoyl)phenyl acetate 4

| Entry No. | Reagent 1 | Reagent 2 | Solvent | Yield |
|---|---|---|---|---|
| 1 | EDCI | Aspirin | DCM | N/A |
| 2 | DCC | Aspirin | DCM | 6% |
| 3 | HATU | Aspirin | DCM | 9% |
| 4 | TEA | Acetic anhydride | DCM | N/R |
| 5 | $H_2SO_4$ | Acetic anhydride | Not used | 39% |

Animal Models

Diabetic Neuropathy Models 65 mg/kg of streptozotocin (Sigma Corp., USA) was dissolved at a concentration of 15 mg/ml in 0.1 M citrate buffer at pH 4.5 and the resulting solution was administered intraperitoneally to mice. Blood glucose levels were measured 1 week after administration and streptozotocin-induced diabetic mice were chosen.

Chemical-Induced Peripheral Neuropathy Models

Vincristine is an anticancer drug that is widely used to treat malignant tumors, including breast cancer, leukemia, lymphoma, and primary brain tumor. However, vincristine was reported to cause neurotoxicity in peripheral nervous fibers and sensory or motor neuropathy after use. The anticancer drug vincristine is known to cause predictable and consistent neurotoxicity in all patients, particularly patients treated with therapeutic doses. When a patient receives a dose of vincristine, paresthesia accompanied by pain is first observed in proportion to the dose. As neuropathy develops, axons are lost together with motor function. Vincristine is also known to induce hypersensitivity of C nerve fiber nociceptors in the peripheral nervous system. Neuropathy was induced by administration of vincristine. First, 0.05 mg/kg of vincristine was administered intraperitoneally. Thereafter, vincristine was administered intraperitoneally twice a week for 6 weeks (0.125 mg/kg each). Neuropathic pain began to appear at week 3 after administration and significant pain was reported at week 4. The degree of neuropathic pain was measured through the tail-flick test (Junzo et al., 2005).

Monosodium Urate (MSU) Models 100 mg of uric acid and 60 μl of 10 N NaOH were dissolved in 20 ml of distilled water and the pH of the solution was adjusted to 7.2-7.4 with HCl (1 N) at 60° C. After stirring at room temperature for 5 days, the solution was plated in a 1 ml tube and stored for 4 days. The solution was vortexed overnight until needle-like crystals appeared. The solution was washed twice with 100% ethanol and centrifuged at 3000 rpm for 2 min. Finally, the MSU crystals were collected and dissolved in 25 μg/μl of endotoxin-free PBS. The resulting sample were injected intra-articularly into mice (MSU 300 μg/10 μl each) under anesthesia. At 24 h post-injection, pain or ankle swelling were measured to determine the analgesic efficacy of a test substance.

Evaluation of Inhibitory Effects of the Compounds 3 and 4 on Inflammation

Experimental Example 1

Measurement of NO Production

Raw 264.7 cells were plated in a 96-well cell culture plate (50,000 cells/well). Lipopolysaccharide (LPS) was diluted to 100 ng/ml and the dilution was added to the cell culture media The LPS stimulus was applied for 24 h to induce the activity of the Raw 264.7 cells and supernatants (50 μl each) obtained from the 96-well cell culture plate were plated in a new plate. 50 μl of a sulfanilamide solution was added and the reaction was allowed to proceed for 10 min. 50 μl of a NED solution was added and the reaction was allowed to proceed for 10 min. The amount of NO produced from the cells in the cell culture media was determined by measuring the absorbance at a wavelength of 540 nm.

As a result, the treatment of Raw 264.7 cells with aspirin and salicylic acid together with LPS (100 ng/ml) was less effective in reducing the production of NO whereas the treatment with 100 μM epinastine was found to reduce the production of NO (FIG. 1). The treatment of Raw 264.7 cells with the compound 3 (E-S) and the compound 4 (E-A) together with LPS (100 ng/ml) led to a concentration-dependent reduction in NO production (FIG. 1 and Table 2). In conclusion, the compound 3 (E-S) and the compound 4 (E-A) was effective in reducing the production of NO compared to the conventional agents, including aspirin, salicylic acid, and epinastine.

TABLE 3

| Compound | 12.5 μM | 25 μM | 50 μM | 100 μM |
|---|---|---|---|---|
| | | Inhibition % | | |
| Aspirin | 0 | 0 | 9.29 | 12.40 |
| Salicylic acid | 0 | 1.27 | 7.18 | 15.64 |
| Epinastine | 0 | 5.48 | 18.73 | 33.40 |
| E-S | 0 | 9.47 | 30.83 | 40.83 |
| E-A | 0 | 17.09 | 40.10 | 52.35 |

Experimental Example 2

Cell Viability Measurement

Raw 264.7 cells were plated in a 96-well cell culture plate (50,000 cells/well). The cell culture media were removed from the 96-well cell culture plate. 100 μl of MTS reagent (CellTiter 96 AQueous One Solution Cell Proliferation Assay, Promega) was added to each well and the reaction was allowed to proceed at 37° C. for 20 min. After the reaction was finished, the cell viability were determined by measuring the absorbance at a wavelength of 490 nm.

Figure 2:
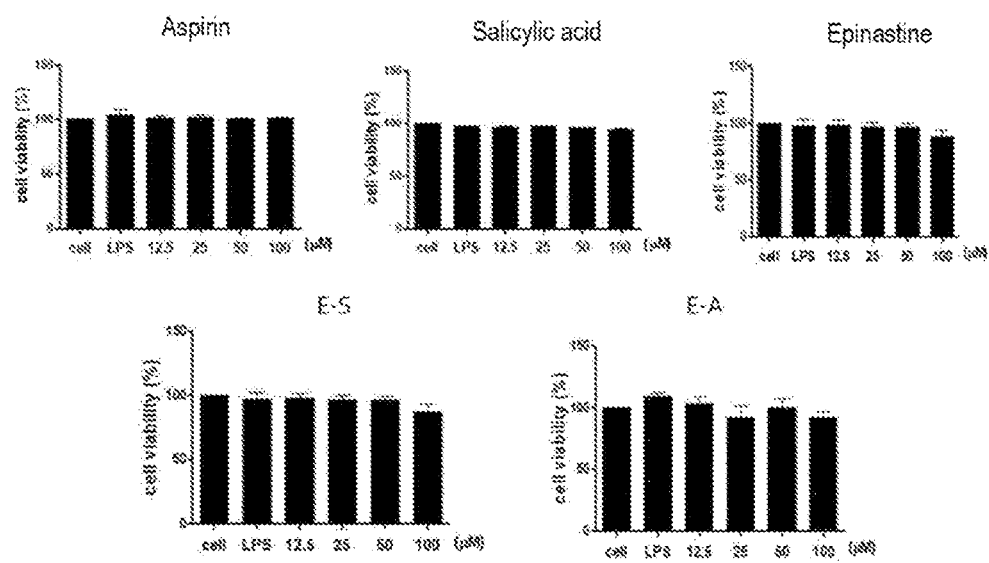
FIG. 2 shows the viabilities of cells when treated with the compounds prepared in Preparative Examples 1 and 2.

As a result, no cell toxicities were observed when treated with aspirin, salicylic acid, epinastine, the compound 3 (E-S), and the compound 4 (E-A) (FIG. 2).

Experimental Example 3

Western Blot Analysis

Cells were harvested, washed with 1×PBS, and suspended by adding a mixture of a protein extraction buffer (150 mM NaCl, 50 mM Tris-HCl pH 7.4, 5 mM EDTA pH 8.0, 1% NP-40) and a protease inhibitor cocktail. Then, the reaction was allowed to proceed in ice for 20 min, sonicated, and centrifuged (13,000 rpm, 30 min). The concentration of proteins in the supernatant was quantified by a BCA protein assay and proteins were separated on the basis of size on an SDS-PAGE gel. Thereafter, proteins were transferred to a PVDF membrane and blocked with skim milk for 1 h. Primary and secondary antibodies were coupled and photosensitized with ECL solution to determine the expression levels of desired proteins.

Figure 3:
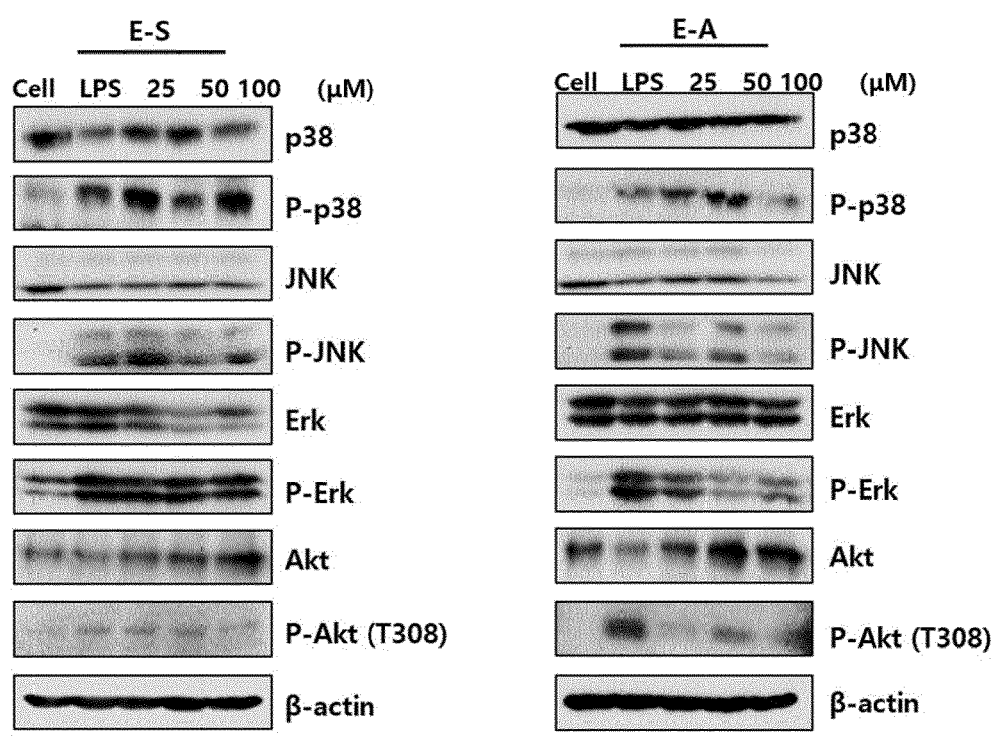
FIG. 3 shows the results of Western blotting when treated with the compounds prepared in Preparative Examples 1 and 2.

As a result, the compound 3 (E-S) did not appear to significantly affect MAPK signaling in the mechanism of inflammatory response by LPS signals but the phosphorylation of Akt by LPS was observed to decrease at 100 uM. The compound 4 E-A was found to affect both MAPK signaling and Akt signaling by LPS signals and reduce the activity of proteins (FIG. 3).

As a result, aspirin and salicylic acid reduced the intracellular production of NO by LPS signals via binding with epinastine. When LPS signals were applied to cells, MAPK and Akt signaling systems for the initial inflammatory response were confirmed. The activity of MAPK or Akt was reduced depending on the concentrations of the two compounds. Thus, sub-signaling mechanisms of inflammatory response were confirmed. In conclusion, the two compounds 3 and 4 inhibit signals in the inflammatory response mechanisms and finally suppressed the inflammatory response.

Evaluation of Inhibitory Effects of the Compounds 3 and 4 on Pain

Experimental Example 4

Writhing Test

In accordance with the most common method for measuring the analgesic efficacies of the test substances in the peripheral nerve based on abdominal contraction responses as indices, 1% acetic acid was administered intraperitoneally to mice to induce damage or pain of the abdominal peripheral vessels. After acetic acid administration, the behavioral profiles of the mice were observed and the numbers of stretching and writhing movements of the mice were counted to determine the analgesic efficacies of the test substances.

Figure 4A:
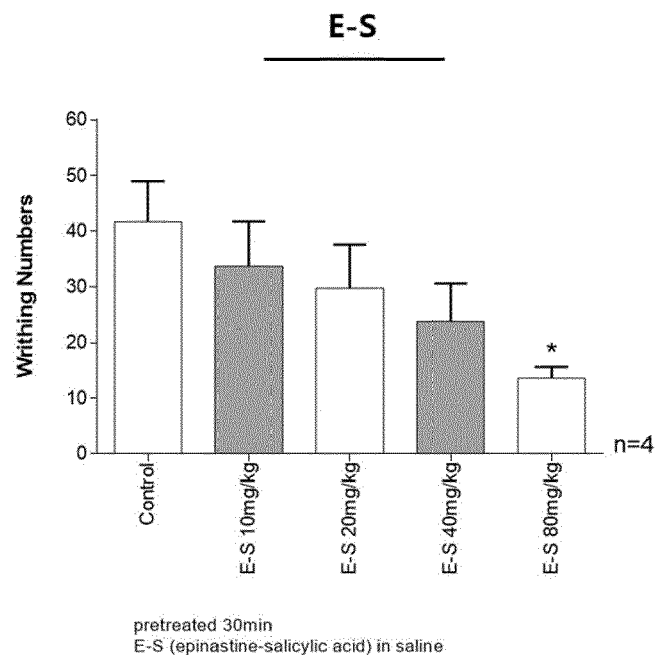
FIG. 4 shows the results of writhing test when treated with the compounds prepared in Preparative Examples 1 and 2.
Figure 4B:
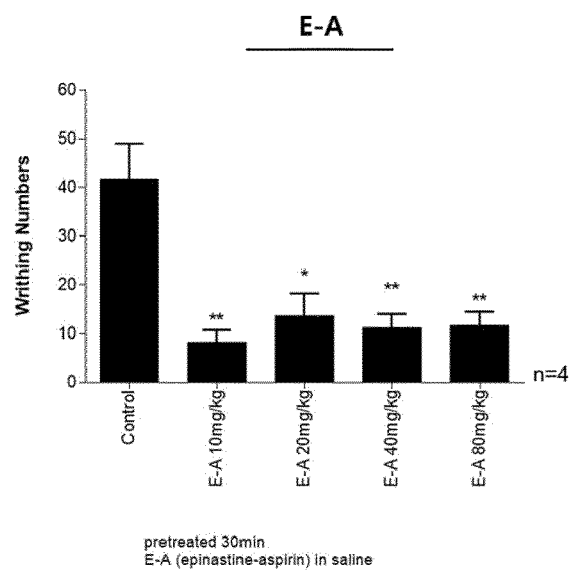

30 min after pretreatment with the compound 3 (E-S) at concentrations of 10, 20, 40, and 80 mg/kg, writhing test was conducted to assess the analgesic efficacy of the compound 3. As a result, the analgesic efficacy of the compound 3 was concentration-dependent (FIG. 4a and Table 4). The analgesic efficacy of the compound 4 (E-A) was assessed in the same manner as that of the compound 3. As a result, the best analgesic efficacy was observed at a concentration of 10 mg/kg (FIG. 4b and Table 5).

TABLE 4

| Control | E-S 10 mg/kg | E-S 20 mg/kg | E-S 40 mg/kg | E-S 80 mg/kg |
|---|---|---|---|---|
| 41.75 | 33.75 | 29.75 | 23.75 | 12.75 |

TABLE 5

| Control | E-A 10 mg/kg | E-A 20 mg/kg | E-A 40 mg/kg | E-A 80 mg/kg |
|---|---|---|---|---|
| 41.75 | 8.25 | 13.75 | 11.25 | 12.25 |

Experimental Example 5

Formalin Test

5% formalin was injected subcutaneously into the soles of the hind feet of mice. The mice licked their soles and shook their paws owing to formalin-induced pain. At 20-40 min post-injection ($2^{nd}$ phase), the mice again licked their soles or shook their paws. Pain felt for 5 min post-injection ($1^{st}$ phase) is the same level as the sensation of pain when the body is harmfully stimulated. Pain between 20 and 40 min ($2^{nd}$ phase) is mainly tonic inflammatory pain and is known to be very similar to pain after a big surgical operation.

Figure 5A:
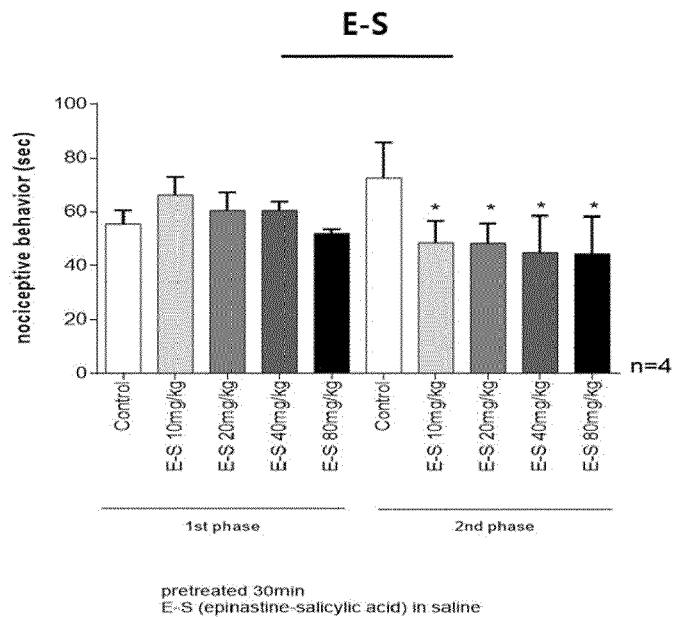
FIG. 5 shows the results of formalin test when treated with the compounds prepared in Preparative Examples 1 and 2.
Figure 5B:
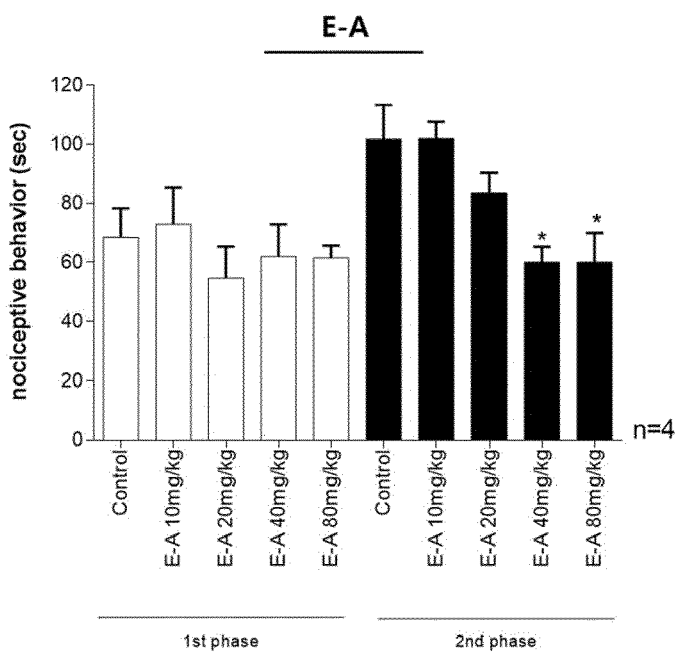

30 min after pretreatment with the compound 3 (E-S) at concentrations of 10, 20, 40, and 80 mg/kg, formalin test was conducted to assess the analgesic efficacy of the compound 3. As a result, the analgesic efficacy of the compound 3 was observed in the $2^{nd}$ phase (FIG. 5a and Table 6). The analgesic efficacy of the compound 4 (E-A) was assessed in the same manner as that of the compound 3. As a result, the analgesic efficacy of the compound 4 (E-A) was observed in the 2n$^d$ phase (FIG. 5b and Table 7).

TABLE 6

| Control | E-S 10 mg/kg | E-S 20 mg/kg | E-S 40 mg/kg | E-S 80 mg/kg | Control | E-S 10 mg/kg | E-S 20 mg/kg | E-S 40 mg/kg | E-S 80 mg/kg |
|---|---|---|---|---|---|---|---|---|---|
| 55.5 | 66.25 | 60.5 | 60.5 | 52.0 | 72.5 | 48.5 | 48.25 | 45.0 | 44.5 |

TABLE 7

| Control | E-A 10 mg/kg | E-A 20 mg/kg | E-A 40 mg/kg | E-A 80 mg/kg | Control | E-A 10 mg/kg | E-A 20 mg/kg | E-A 40 mg/kg | E-A 80 mg/kg |
|---|---|---|---|---|---|---|---|---|---|
| 68.5 | 73.0 | 54.7 | 62.0 | 61.5 | 101.7 | 102.0 | 83.5 | 60.0 | 60.0 |

Experimental Example 6

Hot-Plate Test

Hot-plate test was conducted using an electric heater to measure the analgesic activity of the test substances on the acute thermal stimulus. Experimental animals were injected with the test drugs and a vehicle (control) and were sequentially placed on an electric heater (hot-plate). The response time to the thermal stimulus (−55° C.) was defined as the time until the experimental animal licked their paws. Male mice weighing 22-25 g, aged 4-5 weeks, were used as the test animals (10 per group).

Figure 6A:
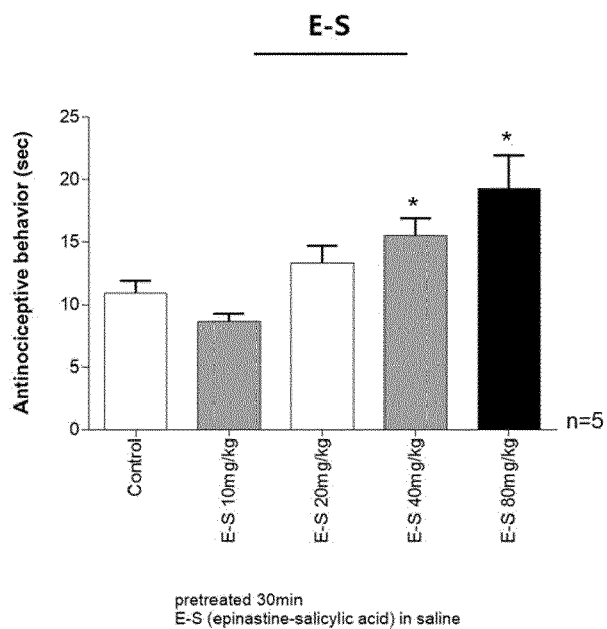
FIG. 6 shows the results of hot-plate test when treated with the compounds prepared in Preparative Examples 1 and 2.
Figure 6B:
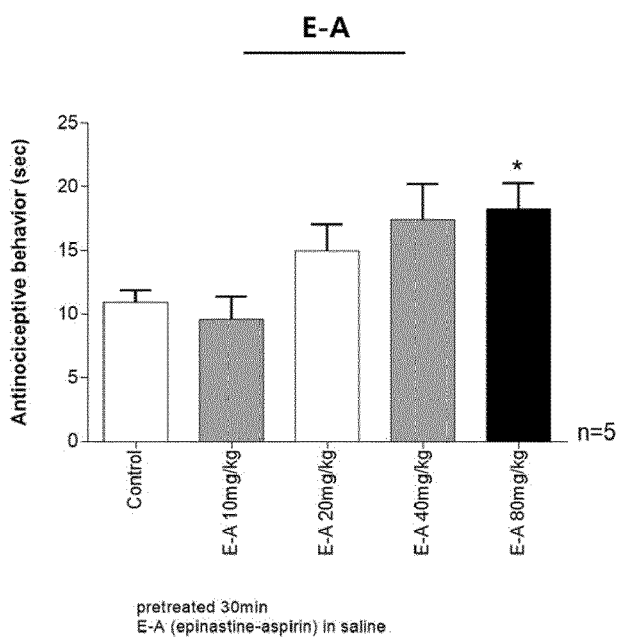

30 min after pretreatment with the compound 3 (E-S) at concentrations of 10, 20, 40, and 80 mg/kg, hot-plate test was conducted to assess the analgesic efficacy of the compound 3. As a result, the analgesic efficacy of the compound 3 was observed to be significant at 40 and 80 mg/kg (FIG. 6a and Table 8). The analgesic efficacy of the compound 4 (E-A) was assessed in the same manner as that of the compound 3. As a result, the analgesic efficacy of the compound 4 (E-A) was observed in the 2$^{nd}$ phase (FIG. 6b and Table 9).

TABLE 8

| Control | E-S 10 mg/kg | E-S 20 mg/kg | E-S 40 mg/kg | E-S 80 mg/kg |
|---|---|---|---|---|
| 10.94 | 8.64 | 13.34 | 15.52 | 19.30 |

TABLE 9

| Control | E-A 10 mg/kg | E-A 20 mg/kg | E-A 40 mg/kg | E-A 80 mg/kg |
|---|---|---|---|---|
| 10.94 | 9.58 | 14.98 | 17.42 | 18.30 |

Experimental Example 7

Von-Frey Test

After damage to the sciatic nerve, allodynia induced by the mechanical stimulus was measured. Mice were housed in acrylic chambers on a steel mesh floor and acclimated for ≥60 min before testing. Continuous responses were evaluated using Von-frey filaments by the up-down method. The filaments were brought into vertical contact with the affected left soles and the contact was maintained for 5-6 sec. The response was considered to be positive when the mouse rapidly avoided the stimulus, startled or licked its sole. The Von-frey filaments were first used to stimulate the mice. When the mouse showed a positive response, it was stimulated with weaker filaments. Alternatively, when the mouse did not show a positive response, it was stimulated with stronger filaments.

Figure 7:
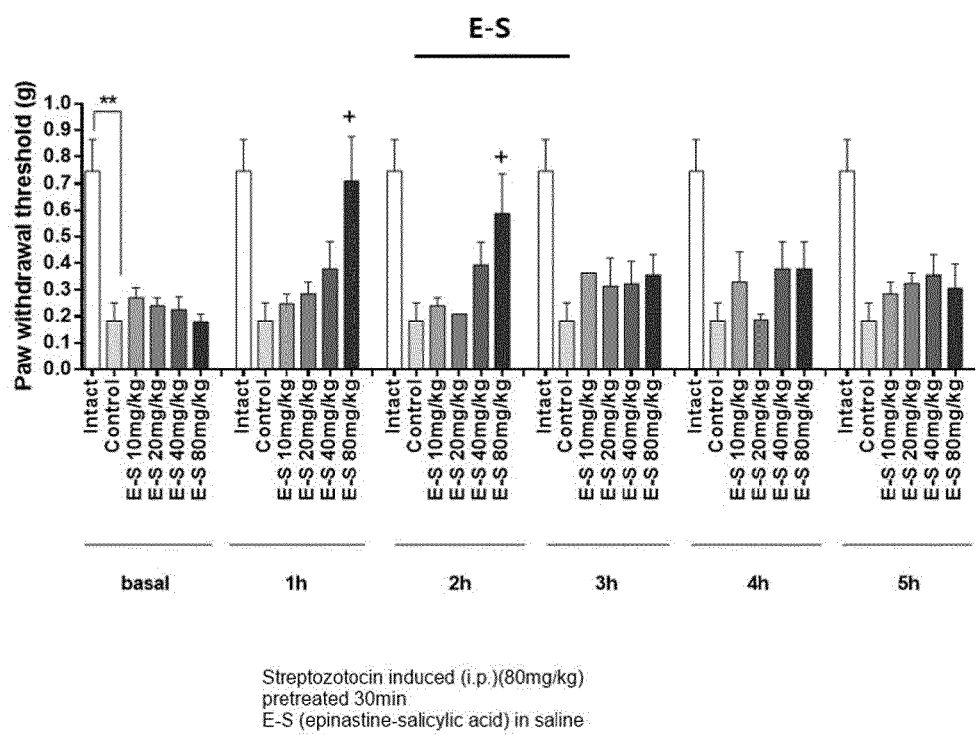
FIG. 7 shows the results of Von-frey test in diabetic neuropathy models when treated with the compound E-S prepared in Preparative Example 1.
Figure 8:
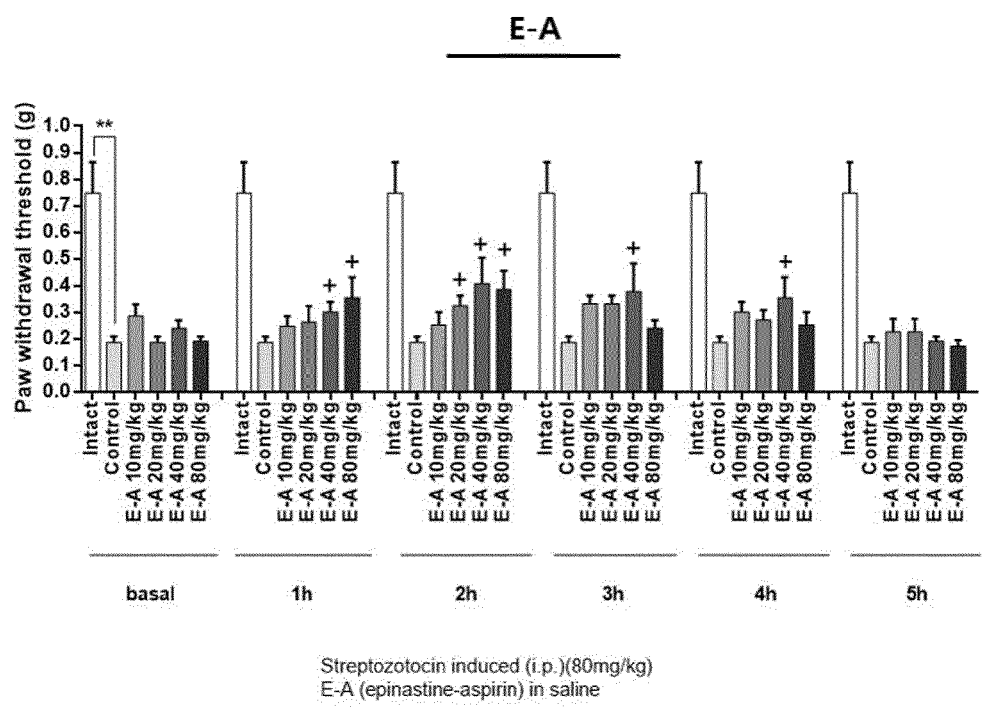
FIG. 8 shows the results of Von-frey test in diabetic neuropathy models when treated with the compound E-A prepared in Preparative Example 2.

The inhibitory effects of the test substances on pain were determined in diabetic neuropathy models. To this end, after oral administration of each test substance at concentrations of 10, 20, 40, and 80 mg/kg, threshold values were measured at different periods of time through Von-frey test. Until 1-2 h after treatment with the compound 3 (E-S), the highest analgesic efficacy of the compound 3 was observed at a concentration of 80 mg/kg. The analgesic efficacy of the compound 3 was concentration-dependent until 1-2 h after treatment, and thereafter, it decreased gradually (FIG. 7 and Table 10). After treatment with the compound 4 (E-A) in the same manner as that with the compound 3, the highest analgesic efficacies of the compound 4 were observed at concentrations of 40 and 80 mg/kg. The analgesic efficacy of the compound 4 was concentration-dependent from 1 h after treatment and was maintained until 3 h after treatment, and thereafter, it decreased gradually (FIG. 8 and Table 11).

TABLE 10

| | | basal | | | | | | 1 h | | | |
|---|---|---|---|---|---|---|---|---|---|---|---|
| Intact | Control | E-S 10 mg/kg | E-S 20 mg/kg | E-S 40 mg/kg | E-S 80 mg/kg | Intact | Control | E-S 10 mg/kg | E-S 20 mg/kg | E-S 40 mg/kg | E-S 80 mg/kg |
| 0.747 | 0.183 | 0.247 | 0.208 | 0.225 | 0.164 | 0.747 | 0.183 | 0.247 | 0.286 | 0.314 | 0.613 |
| | | 2 h | | | | | | 3 h | | | |
| Intact | Control | E-S 10 mg/kg | E-S 20 mg/kg | E-S 40 mg/kg | E-S 80 mg/kg | Intact | Control | E-S 10 mg/kg | E-S 20 mg/kg | E-S 40 mg/kg | E-S 80 mg/kg |
| 0.747 | 0.183 | 0.208 | 0.208 | 0.391 | 0.574 | 0.747 | 0.183 | 0.363 | 0.314 | 0.352 | 0.391 |

TABLE 10-continued

| | | 4 h | | | | | | 5 h | | | |
|---|---|---|---|---|---|---|---|---|---|---|---|
| Intact | Control | E-S 10 mg/kg | E-S 20 mg/kg | E-S 40 mg/kg | E-S 80 mg/kg | Intact | Control | E-S 10 mg/kg | E-S 20 mg/kg | E-S 40 mg/kg | E-S 80 mg/kg |
| 0.747 | 0.183 | 0.330 | 0.186 | 0.314 | 0.419 | 0.747 | 0.183 | 0.286 | 0.324 | 0.391 | 0.225 |

TABLE 11

| | | basal | | | | | | 1 h | | | |
|---|---|---|---|---|---|---|---|---|---|---|---|
| Intact | Control | E-A 10 mg/kg | E-A 20 mg/kg | E-A 40 mg/kg | E-A 80 mg/kg | Intact | Control | E-A 10 mg/kg | E-A 20 mg/kg | E-A 40 mg/kg | E-A 80 mg/kg |
| 0.747 | 0.186 | 0.286 | 0.186 | 0.247 | 0.208 | 0.747 | 0.186 | 0.260 | 0.263 | 0.286 | 0.391 |
| | | 2 h | | | | | | 3 h | | | |
| Intact | Control | E-A 10 mg/kg | E-A 20 mg/kg | E-A 40 mg/kg | E-A 80 mg/kg | Intact | Control | E-A 10 mg/kg | E-A 20 mg/kg | E-A 40 mg/kg | E-A 80 mg/kg |
| 0.747 | 0.184 | 0.263 | 0.324 | 0.458 | 0.391 | 0.747 | 0.186 | 0.324 | 0.321 | 0.419 | 0.247 |
| | | 4 h | | | | | | 5 h | | | |
| Intact | Control | E-A 10 mg/kg | E-A 20 mg/kg | E-A 40 mg/kg | E-A 80 mg/kg | Intact | Control | E-A 10 mg/kg | E-A 20 mg/kg | E-A 40 mg/kg | E-A 80 mg/kg |
| 0.747 | 0.186 | 0.286 | 0.247 | 0.391 | 0.286 | 0.747 | 0.186 | 0.225 | 0.225 | 0.186 | 0.186 |

Figure 9:
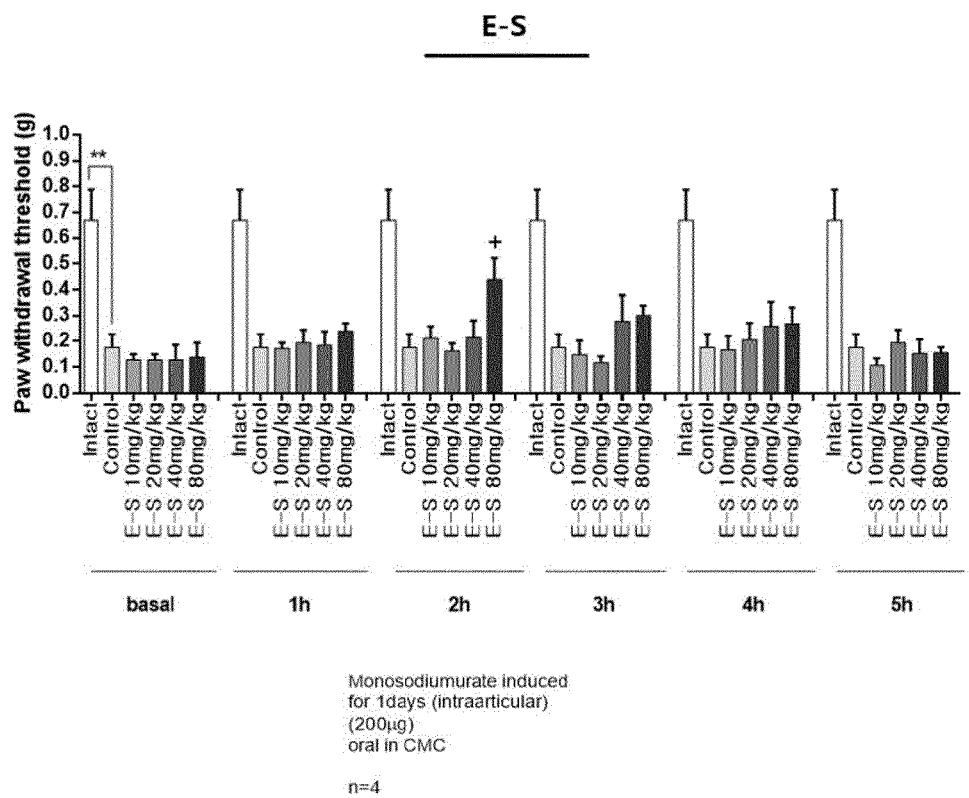
FIG. 9 shows the results of Von-frey test in monosodium urate models when treated with the compound E-S prepared in Preparative Example 1.
Figure 10:
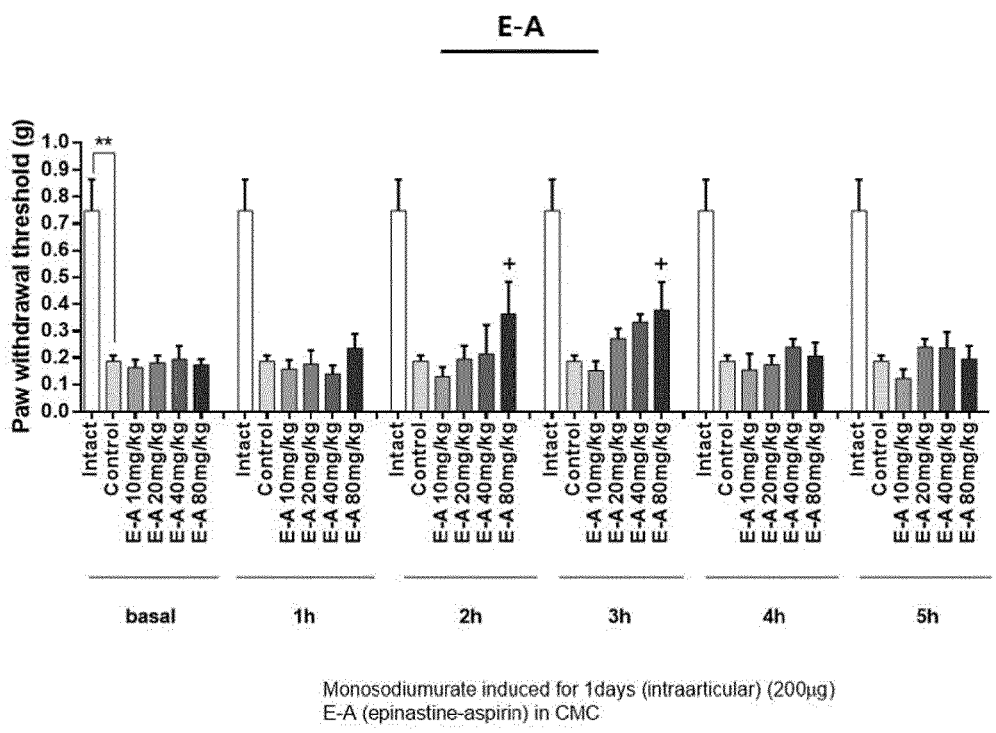
FIG. 10 shows the results of Von-frey test in monosodium urate models when treated with the compound E-A prepared in Preparative Example 2.

The analgesic efficacies of the test substances were evaluated in monosodium urate models. To this end, after oral administration of each test substance at concentrations of 10, 20, 40, and 80 mg/kg, threshold values were measured at different periods of time through Von-frey test. 2 h after treatment with the compound 3 (E-S), the highest analgesic efficacy of the compound 3 was observed at a concentration of 80 mg/kg. The analgesic efficacy of the compound 3 was concentration-dependent until 2 h after treatment, and thereafter, it decreased gradually (FIG. 9 and Table 12). Until 2-3 h after treatment with the compound 4 (E-A) in the same manner as that with the compound 3, the highest analgesic efficacy of the compound 4 was observed at a concentration of 80 mg/kg. The analgesic efficacy of the compound 4 was concentration-dependent until 2-3 h after treatment, and thereafter, it decreased gradually (FIG. 10 and Table 13).

TABLE 12

| | | Basal | | | | | | 1 h | | | |
|---|---|---|---|---|---|---|---|---|---|---|---|
| Intact | Control | E-S 10 mg/kg | E-S 20 mg/kg | E-S 40 mg/kg | E-S 80 mg/kg | Intact | Control | E-S 10 mg/kg | E-S 20 mg/kg | E-S 40 mg/kg | E-S 80 mg/kg |
| 0.670 | 0.176 | 0.127 | 0.127 | 0.127 | 0.138 | 0.670 | 0.176 | 0.173 | 0.194 | 0.183 | 0.239 |
| | | 2 h | | | | | | 3 h | | | |
| Intact | Control | E-S 10 mg/kg | E-S 20 mg/kg | E-S 40 mg/kg | E-S 80 mg/kg | Intact | Control | E-S 10 mg/kg | E-S 20 mg/kg | E-S 40 mg/kg | E-S 80 mg/kg |
| 0.670 | 0.176 | 0.211 | 0.163 | 0.214 | 0.439 | 0.670 | 0.176 | 0.148 | 0.117 | 0.278 | 0.301 |
| | | 4 h | | | | | | 5 h | | | |
| Intact | Control | E-S 10 mg/kg | E-S 20 mg/kg | E-S 40 mg/kg | E-S 80 mg/kg | Intact | Control | E-S 10 mg/kg | E-S 20 mg/kg | E-S 40 mg/kg | E-S 80 mg/kg |
| 0.670 | 0.176 | 0.166 | 0.207 | 0.257 | 0.267 | 0.670 | 0.176 | 0.107 | 0.194 | 0.152 | 0.155 |

TABLE 13

| | basal | | | | | | 1 h | | | | |
|---|---|---|---|---|---|---|---|---|---|---|---|
| Intact | Control | E-A 10 mg/kg | E-A 20 mg/kg | E-A 40 mg/kg | E-A 80 mg/kg | Intact | Control | E-S 10 mg/kg | E-S 20 mg/kg | E-S 40 mg/kg | E-S 80 mg/kg |
| 0.747 | 0.186 | 0.186 | 0.208 | 0.190 | 0.186 | 0.747 | 0.186 | 0.166 | 0.203 | 0.144 | 0.203 |
| | 2 h | | | | | | 3 h | | | | |
| Intact mg/kg | Control mg/kg | E-S 10 mg/kg | E-S 20 mg/kg | E-S 40 mg/kg | E-S 80 mg/kg | Intact mg/kg | Control mg/kg | E-S 10 | E-S 20 | E-S 40 | E-S 80 |
| 0.747 | 0.186 | 0.109 | 0.212 | 0.237 | 0.362 | 0.747 | 0.186 | 0.151 | 0.247 | 0.324 | 0.314 |
| | 4 h | | | | | | 5 h | | | | |
| Intact | Control | E-S 10 mg/kg | E-S 20 mg/kg | E-S 40 mg/kg | E-S 80 mg/kg | Intact | Control | E-S 10 mg/kg | E-S 20 mg/kg | E-S 40 mg/kg | E-S 80 mg/kg |
| 0.747 | 0.186 | 0.102 | 0.173 | 0.247 | 0.205 | 0.747 | 0.186 | 0.122 | 0.247 | 0.286 | 0.190 |

Figure 11:
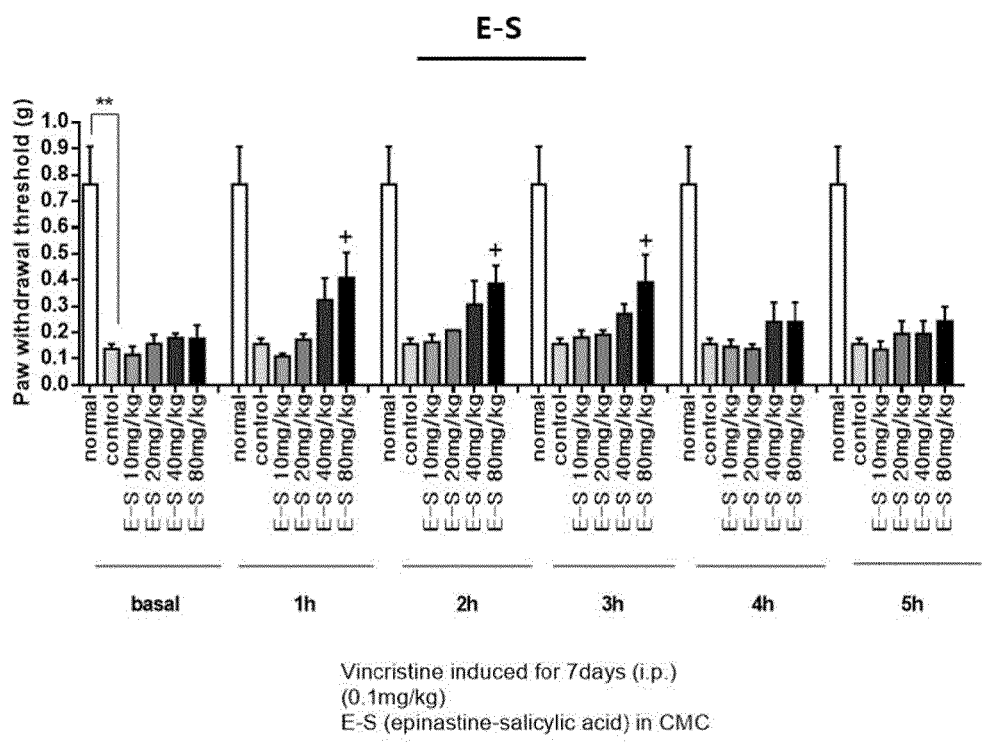
FIG. 11 shows the results of Von-frey test in anticancer drug-induced peripheral neuropathy models when treated with the compound E-S prepared in Preparative Example 1.

The analgesic efficacies of the test substances were evaluated in anticancer drug-induced peripheral neuropathy models. To this end, after oral administration of each test substance at concentrations of 10, 20, 40, and 80 mg/kg, threshold values were measured at different periods of time through Von-frey test. 1 h after treatment with the compound 3 (E-S), the highest analgesic efficacy of the compound 3 was observed at a concentration of 80 mg/kg. The analgesic efficacy of the compound 3 was concentration-dependent until 1 h after treatment and was maintained until 3 h after treatment, and thereafter, it decreased gradually (FIG. 11 and Table 14).

The invention claimed is:
1. A compound represented by Formula A:

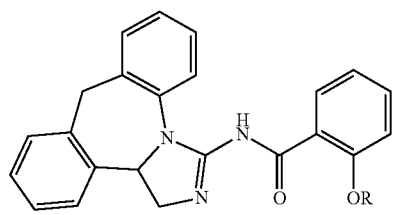

Formula A or a pharmaceutically acceptable salt thereof, wherein:
R is H, $C_1$-$C_5$ alkyl, or $C(O)C_1$-$C_5$ alkyl.

TABLE 14

| | Basal | | | | | | 1 h | | | | |
|---|---|---|---|---|---|---|---|---|---|---|---|
| normal | control | E-S 10 mg/kg | E-S 20 mg/kg | E-S 40 mg/kg | E-S 80 mg/kg | normal | control | E-S 10 mg/kg | E-S 20 mg/kg | E-S 40 mg/kg | E-S 80 mg/kg |
| 0.763 | 0.137 | 0.113 | 0.157 | 0.173 | 0.176 | 0.763 | 0.155 | 0.110 | 0.173 | 0.324 | 0.408 |
| | 2 h | | | | | | 3 h | | | | |
| normal | control | E-S 10 mg/kg | E-S 20 mg/kg | E-S 40 mg/kg | E-S 80 mg/kg | normal | control | E-S 10 mg/kg | E-S 20 mg/kg | E-S 40 mg/kg | E-S 80 mg/kg |
| 0.763 | 0.155 | 0.163 | 0.208 | 0.306 | 0.385 | 0.763 | 0.155 | 0.180 | 0.191 | 0.270 | 0.390 |
| | 4 h | | | | | | 5 h | | | | |
| normal | control | E-S 10 mg/kg | E-S 20 mg/kg | E-S 40 mg/kg | E-S 80 mg/kg | normal | control | E-S 10 mg/kg | E-S 20 mg/kg | E-S 40 mg/kg | E-S 80 mg/kg |
| 0.763 | 0.155 | 0.145 | 0.137 | 0.239 | 0.239 | 0.763 | 0.155 | 0.135 | 0.194 | 0.194 | 0.242 |

2. The compound according to claim 1, wherein the compound is selected from the group consisting of:

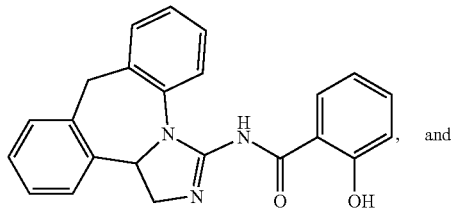
(E-S)
, and

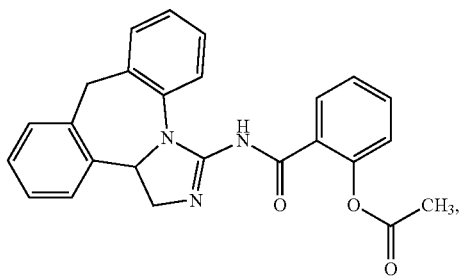
(E-A)

or a pharmaceutically acceptable salt thereof.

3. A method for treating inflammation in a subject, wherein the method comprises administering to the subject in need thereof a therapeutically effective amount of the compound according to claim 1, or a pharmaceutically acceptable salt thereof.

4. A method for treating pain in a subject, wherein the method comprises administering to the subject in need thereof a therapeutically effective amount of the compound according to claim 1, or a pharmaceutically acceptable salt thereof.

5. The method according to claim 4, wherein the pain is selected from the group consisting of cancer pain, idiopathic pain, inflammatory pain, invasive pain, migraine, neuropathic pain, nociceptive pain, pathologic pain, post-operative pain, psychogenic pain, and trigeminal neuralgia.

6. The method according to claim 5, wherein the neuropathic pain is diabetic neuropathic pain.

7. A process for preparing a compound represented by Formula 3:

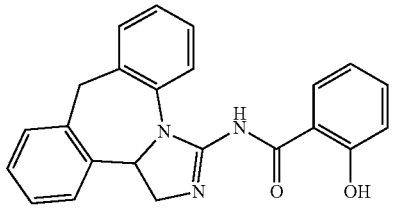
Formula 3 wherein the process comprises:
reacting a compound represented by Formula 2:

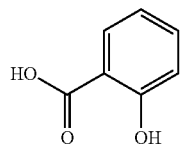
Formula 2 with a compound represented by Formula 1:

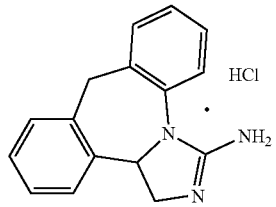
Formula 1 in the presence of a solvent, a base, and a coupling agent.

8. The process according to claim 7, wherein the solvent is selected from the group consisting of acetonitrile, chloroform, and dichloromethane.

9. The process according to claim 7, wherein the base is selected from the group consisting of N,N-diisopropylethylamine and triethylamine.

10. The process according to claim 7, wherein the coupling agent is selected from the group consisting of N,N'-dicyclohexylcarbodiimide, (1-[bis(dimethylamino)methylene]-1H-1,2,3-triazolo[4,5-b]pyridinium 3-oxide hexafluorophosphate), and 1-ethyl-3-(3-dimethylaminopropyl)carbodiimide.

* * * * *